United States Patent [19]

Asahi et al.

[11] Patent Number: 4,894,434

[45] Date of Patent: Jan. 16, 1990

[54] POLYCYANOARYL THIOETHER AND PREPARATION THEREOF

[75] Inventors: Tetsuya Asahi; Yozo Kondo, both of Mie, Japan

[73] Assignee: Tosoh Corporation, Yamaguchi, Japan

[21] Appl. No.: 195,927

[22] Filed: May 19, 1988

[30] Foreign Application Priority Data

May 20, 1987 [JP] Japan ................... 62-121392

[51] Int. Cl.$^4$ .............................. C08G 75/14
[52] U.S. Cl. ........................ 528/388; 525/537
[58] Field of Search ........................ 528/388

[56] References Cited

U.S. PATENT DOCUMENTS

| | | |
|---|---|---|
| 3,354,129 | 11/1967 | Edmonds et al. |
| 3,987,016 | 10/1976 | Haddad et al. |
| 4,440,915 | 4/1984 | Asakura et al. .............. 528/388 |
| 4,537,953 | 8/1985 | Kawakami et al. ........... 528/388 |
| 4,605,713 | 8/1986 | Heitz et al. .................. 525/537 |

FOREIGN PATENT DOCUMENTS 53344 6/1982 European Pat. Off.
108682 5/1984 European Pat. Off.

OTHER PUBLICATIONS

Chem. Ab., vol. 86, No. 4, p. 25 (1–1977).

*Primary Examiner*—John C. Bleutge
*Assistant Examiner*—David W. Woodward
*Attorney, Agent, or Firm*—Sughrue, Mion, Zinn, Macpeak & Seas

[57] ABSTRACT

A highly heat resistant polymer, polycyanoaryl thioether, of formula:

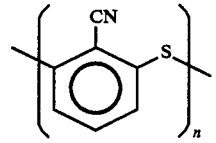

where n is a number of not less than 3 is disclosed. A process for preparing the novel polymer is also disclosed.

5 Claims, No Drawings

POLYCYANOARYL THIOETHER AND PREPARATION THEREOF

FIELD OF THE INVENTION

This invention relates to a novel polymeric substance and preparation thereof and, particularly, to polycyanoaryl thioether having an excellent heat resistance which permits the polymer to be advantageously employed in the industrial fields of manufacturing parts, for example, of electronic instruments, transportation vehicles and aircrafts, and a process for preparing the novel polymer.

BACKGROUND OF THE INVENTION

Japanese Patent Publication (KOKOKU) No. 45-3368 (published in 1970) discloses polyaryl thioethers of various structures. Japanese Patent Application Public Disclosure (KOKAI) Nos. 47-14270 and 59-206433 (laid open in 1972 and 1984, respectively) describe polycyanoaryl ethers of various structures.

However, any polycyanoaryl thioether possessing the structural characteristics of polyaryl thioether simultaneously with the structural characteristics of polycyanoaryl ether in each of the repeating units constituting the backbone has not yet been reported. Consequently, any process for producing polycyanoaryl thioether has not been accomplished.

SUMMARY OF THE INVENTION

It is an object of the present invention is to provide a novel resin, polycyanoaryl thioether, having an excellent heat resistance resulting from the existence of the structural characteristics of polyaryl thioether simultaneously with the structural characteristics of polycyanoaryl ether in each of the repeating units constituting the backbone.

Another object of the invention is to provide such a novel polymer resin which is advantageously employed particularly in the fields of manufacturing electronics instruments, transportation vehicles and aircrafts.

A further object of the invention is to provide a process for preparing the novel polymer.

Accordingly, the present invention provides a novel polymer, polycyanoaryl thioether, represented by formula (I):

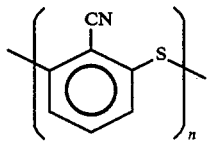
(I)

where n is a number of not less than 3. The novel polymer possesses the structural characteristics of polyaryl thioether and the structural characteristics of polycyanoaryl ether in each of the repeating units. The polymer has been found to be excellently heat resistant.

Further, the invention provides a process for preparing the novel polymer, polycyanoaryl thioether, of formula (I), which comprises reacting 2,6-dihalogenobenzonitrile with a sulfiding agent in an organic solvent. This process is readily feasible in commercial practice because of its simplicity and high reliability.

Examples of the 2,6-dihalogenobenzonitriles which may be used in the present process include 2,6-difluoro-, 2,6-dichloro-, 2,6-dibromo- and 2,6-di-iodo-benzonitriles.

Alkali metal sulfides and combinations of sulfur sources with alkali metal hydroxides may be mentioned as the sulfiding agent employed in the process. Examples of the alkali metal sulfides include sulfides of lithium, sodium, potassium, rubidium and cesium and mixtures thereof. Examples of the sulfur sources include alkali metal hydrosulfides, thioamide hydrogensulfides, thiourea, thiocarbamate, thiocarboxylic acids, carbon disulfide, thiocarboxylates, sulfur (elementary) and phosphorus pentasulfide. Particular examples of the alkali metal hydrosulfides include hydrosulfides of lithium, sodium, potassium, rubidium and cesium and mixtures thereof. Examples of the alkali metal hydroxides include hydroxides of potassium, sodium, lithium and cesium and mixtures thereof, with sodium hydroxide most preferred.

Generally, the present process for the preparation of polycyanoaryl thioether by reaction between the 2,6-dihalogenobenzonitrile and the sulfiding agent may be conducted in an anhydrous organic solvent under a stream of an inert gas, for example nitrogen, while heating the reactants at temperatures of from about 20° C. to about 200° C. for a period of from about 1 to about 20 hours.

The molar ratio of the sulfur (calculated as S) to the 2,6-dihalogenobenzonitrile employed in the process may range from about 0.7:1 to about 1.30:1, and preferably the molar ratio is substantially unity (1), especially in the range of from 0.95:1 to 1.10:1.

In general, a concentration of from about 50 to about 400 grams of the monomeric reactants (i.e. the 2,6-dihalogenobenzonitrile plus the sulfiding agent) per liter of the solvent is conveniently selected to be kept during the reaction period.

Examples of the organic solvents which may be employed in the present process include amide solvents, such as N,N-dimethyl formamide, N,N-dimethyl acetamide, and N-methyl-2-pyrrolidone; organic sulfur-containing solvents such as dimethyl sulfoxide, diphenyl sulfone, and sulfolane; and benzene solvents such as nitrobenzene.

EXAMPLES

The invention will be further described with reference to the following Examples. However, the Examples are for illustrative purpose only and details contained therein should not be considered as limitations on the present invention.

EXAMPLE 1

Polycyanoaryl thioether of formula (I) was prepared as follows:

A 200 ml-flask provided with a stirrer, a thermometer and an inlet for nitrogen was charged with 2.40 g of sodium sulfide nonahydrate (0.01 mole) and 80 ml of N-methyl-2-pyrrolidone. The mixture was heated to 200° C. under a nitrogen blanket so as to remove water by azeotropic distillation. Thereafter, 1.72 g of 2,6-dichlorobenzonitrile (0.01 mole) was added to the dehydrated mixture and the heating was continued for a further 6 hours with stirring.

At the end of the heating time, the reaction mixture was cooled to room temperature and poured into one liter of methanol. Then the mixture was filtered and the solid product was washed with acetone and water several times and dried in vacuo at 120° C. for 16 hours to give a pale brown powder at a yield of 1.26 g (95% based on the starting material used).

The product resin showed a reduced viscosity ($\eta$sp/c) of 0.40 as measured using a solution of the resin in concenntrated sulfuric acid (0.5 g resin/dl conc. sulfuric acid) at 140° C.

Infrared adsorption spectrum (by the KBr-tablet technique) of a sample of the product resin showed the following adsorptions specific to polycyanoaryl thioether: 3030 cm$^{-1}$ and 830 cm$^{-1}$, C—H bonds in benzene ring; 1590 cm$^{-1}$, C—C bonds in benzene ring; 2220 cm$^{-1}$, cyano (or nitrile) group; 1095 cm$^{-1}$ and 735 cm$^{-1}$, thioether group.

By elementary analysis of the resin gave the following results:

|  | C | H | N | S |
|---|---|---|---|---|
| Theory (%) | 63.16 | 2.26 | 10.53 | 24.05 |
| Analysis (%) | 62.98 | 2.03 | 10.47 | 24.52 |

By thermal analysis, the product was found to have a melting point of 400° C., a glass transition temperature of 167° C. and a thermal decomposition temperature of 540° C., representing an unexpectedly excellent heat resistance of the resin.

Up to date, no solvents other than a hot concentrated sulfuric acid have been found to be effective for dissolving this product resin.

EXAMPLE 2

The procedure as described in Example 1 was repeated using 1.39 g of 2,6-difluorobenzonitrile (0.01 mole) and 2.40 g of sodium sulfide nonahydrate (0.01 mole) to give a yield of 1.27 g of a pale brown powder (96% based on the starting material used).

The product resin showed a reduced viscosity ($\eta$sp/c) of 0.73 as measured using a solution of the resin in concenntrated sulfuric acid (0.5 g resin/dl conc. sulfuric acid at 140° C.).

Infrared adsorption spectrum (by the Kbr-tablet technique) of the resin showed adsorptions specific to polycyanoaryl thioether at 3030 cm$^{-1}$, 2220 cm$^{-1}$, 1590 cm$^{-1}$, 1095 cm$^{-1}$, 830 cm$^{-1}$ and 735 cm$^{-1}$ similarly to those in Example 1.

Elementary analysis of the resin gave the following results:

|  | C | H | N | S |
|---|---|---|---|---|
| Theory (%) | 63.16 | 2.26 | 10.53 | 24.05 |
| Analysis (%) | 63.01 | 2.31 | 10.19 | 24.49 |

By thermal analysis, the product was found to have a melting point of 460° C., a glass transition temperature of 173° C. and a thermal decomposition temperature of 560° C., representing an unexpectedly excellent heat resistance.

Up to date, no solvents other than a hot concentrated sulfuric acid have been found to be effective for dissolving the product of this Example.

From the above disclosure, it will be appreciated that the present invention provides a novel, highly heat resistant polycyanoaryl thioether resin of formula (I) which is characterized by possessing the structural characteristics of polyaryl thioether simultaneously with the structural characteristics of polycyanoaryl ether and also that the present invention provides a commercially feasible process for preparing the novel resin.

The novel polymer according to the present invention may be useful as a raw material for manufacturing industrial parts in the fields of, for example, electronics, transportation vehicle and aircraft industries. The polymer is expected to find its applications in many other fields.

What is claimed is:

1. A polycyanoaryl thioether having a melting point of from 400°–460° C., represented by formula:

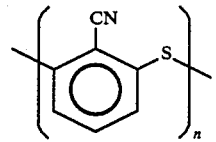

where n is a number of not less than 3.

2. Articles made of a polycyanoaryl thioether, as claimed in claim 1.

3. An article according to claim 2 which is a part of electronic instruments.

4. An article according to claim 2 which is a part of transportation vehicles.

5. An article according to claim 2 which is a part of aircrafts.

* * * * *